United States Patent
Irani et al.

(10) Patent No.: US 7,634,946 B2
(45) Date of Patent: Dec. 22, 2009

(54) TESTING OF BOTTOMHOLE SAMPLERS USING ACOUSTICS

(75) Inventors: Cyrus Irani, Houston, TX (US); Mustafa Hakimuddin, Katy, TX (US)

(73) Assignee: Halliburton Energy Services, Inc., Houston, TX (US)

(*) Notice: Subject to any disclaimer, the term of this patent is extended or adjusted under 35 U.S.C. 154(b) by 6 days.

(21) Appl. No.: 12/124,233

(22) Filed: May 21, 2008

(65) Prior Publication Data

US 2008/0216577 A1    Sep. 11, 2008

Related U.S. Application Data

(60) Division of application No. 11/811,654, filed on Nov. 20, 2006, now Pat. No. 7,395,712, which is a continuation of application No. 10/936,867, filed on Sep. 9, 2004, now abandoned.

(60) Provisional application No. 60/554,479, filed on Mar. 19, 2004.

(51) Int. Cl.
    *E21B 49/02* (2006.01)
(52) U.S. Cl. .......... 73/597; 73/152.28; 73/152.23
(58) Field of Classification Search .......... 73/152.28, 73/152.08, 152.13, 152.18, 152.23, 597
    See application file for complete search history.

(56) References Cited

U.S. PATENT DOCUMENTS

| 4,520,654 | A | 6/1985 | Tehune |
| 4,522,068 | A | 6/1985 | Smith |
| 4,770,043 | A | 9/1988 | Cobb et al. |
| 5,130,950 | A | 7/1992 | Orban et al. |
| 5,178,005 | A | * | 1/1993 | Peterson ............ 73/152.11 |
| 5,214,251 | A | 5/1993 | Orban et al. |
| 5,255,564 | A | 10/1993 | Glad et al. |
| 5,289,875 | A | 3/1994 | Stokley et al. |
| 5,354,956 | A | 10/1994 | Orban et al. |
| RE34,975 | E | 6/1995 | Orban et al. |
| 5,760,297 | A | 6/1998 | Weerstra |
| 5,804,698 | A | 9/1998 | Belonenko et al. |
| 5,886,262 | A | 3/1999 | Sinha |

(Continued)

FOREIGN PATENT DOCUMENTS

EP    1 205 748 A1    5/2002

(Continued)

OTHER PUBLICATIONS

EPO International Search Report for Application No. GB0505434.1, Dated Jun. 10, 2005 (2 Pages).

(Continued)

*Primary Examiner*—Hezron Williams
*Assistant Examiner*—Nashmiya S Fayyaz
(74) *Attorney, Agent, or Firm*—Mark E. Scott

(57) ABSTRACT

A method for testing a hydrocarbon sample. In one embodiment, the apparatus comprises a sheath disposed about the hydrocarbon sample. The apparatus further comprises at least one set of acoustic sensors, wherein the at least one set of acoustic sensors is secured to the sheath, and further wherein at least one set of acoustic sensors produces an acoustic signal having a velocity through the hydrocarbon sample. In addition, the velocity is measured to provide information about the hydrocarbon sample. In other embodiments, the at least one set of acoustic sensors is disposed radially about the hydrocarbon sample.

13 Claims, 2 Drawing Sheets

U.S. PATENT DOCUMENTS

| | | |
|---|---|---|
| 5,984,023 A | 11/1999 | Sharma et al. |
| 6,003,620 A | 12/1999 | Sharma et al. |
| 6,176,323 B1 | 1/2001 | Weirich et al. |
| 6,220,371 B1 | 4/2001 | Sharma et al. |
| 6,230,557 B1 | 5/2001 | Ciglenec et al. |
| 6,295,873 B1 | 10/2001 | Condreva |
| 6,354,146 B1 | 3/2002 | Birchak et al. |
| 6,655,457 B1 | 12/2003 | Dybdahl |
| 6,843,101 B2 | 1/2005 | Hok |
| 6,920,399 B2 | 7/2005 | Priev et al. |
| 6,862,920 B2 | 5/2008 | Gysling et al. |
| 2002/0134144 A1 | 9/2002 | Gysling et al. |
| 2003/0033866 A1* | 2/2003 | Diakonov et al. ........ 73/152.18 |
| 2003/0150262 A1 | 8/2003 | Han et al. |
| 2004/0226386 A1 | 11/2004 | Gysling et al. |

FOREIGN PATENT DOCUMENTS

| | | |
|---|---|---|
| GB | 2376300 A | 12/2002 |

OTHER PUBLICATIONS

Search Report Issued From French Patent Office for French Application No. 0502663 Mailed Jul. 5, 2006 (3 Pages).

* cited by examiner

US 7,634,946 B2

TESTING OF BOTTOMHOLE SAMPLERS USING ACOUSTICS

CROSS-REFERENCE TO RELATED APPLICATIONS

This application is a divisional of application Ser. No. 11/811,654 filed Nov. 20, 2006 titled "Testing of bottomhole samplers using acoustics", now U.S. Pat. No. 7,395,712, which application was a continuation of application Ser. No. 10/936,867 filed Sep. 9, 2004 now abandoned titled "Testing of bottomhole samplers using acoustics", which application claimed the benefit of provisional application No. 60/554,479, filed Mar. 19, 2004. All these applications are incorporated by reference herein as if reproduced in full below.

STATEMENT REGARDING FEDERALLY SPONSORED RESEARCH OR DEVELOPMENT

Not applicable.

BACKGROUND OF THE INVENTION

1. Field of the Invention

This invention relates to the field of testing fluid samples and more specifically to testing hydrocarbon samples using acoustic signals.

2. Background of the Invention

There are pressing needs for inexpensive real time interpretation of hydrocarbon samples collected in bottom hole samplers. Typically, a hydrocarbon sample is collected from an underground reservoir primarily for establishing its pressure-volume-temperature (PVT) and flow assurance properties such as the onset of solids.

PVT information about a hydrocarbon sample can include many different types of information. An important type of information is constant composition expansion (CCE) study, which is sometimes referred to as constant mass expansion (CME). In a typical laboratory conducted CCE study, a sample at reservoir temperature or any secondary temperature is taken to a pressure considerably above reservoir and saturation pressures. The sample is then equilibrated, and the pressure is lowered at constant temperature. As the pressure is lowered, the pressure/volume behavior of the sample is recorded. The sample composition does not change during the exercise. The CCE study typically provides the following data about the sample. In the single phase region, the fluid phase compressibility is established, the saturation pressure (bubble/dew point) is recorded at a lower pressure, and the relative volumes of the various phases are reported at pressures below the saturation pressure. The data generated during a CCE study can be important in that it provides a data set that can be effectively used to tune a compositional Equation of State (EOS), which can improve the complete PVT predictions generated. The collection of CCE data at different temperatures can be even more valuable for tuning purposes.

From a flow assurance standpoint, other important information includes the onset of solids formation in the well string and transport lines. Solids primarily take the form of wax and/or asphaltene particles. Wax particles are high molecular weight paraffinic species that precipitate primarily due to temperature drop and can curtail production operations by agglomeration, sticking to pipe walls, congealing in flow lines, and the like. Asphaltenes tend to have a more complex chemical nature than wax and form primarily due to a disruption in a fine balance of interactions that keep them in suspension/solution in the bulk crude. Asphaltene precipitation is usually preceded by a drop in system pressure that leads to gas release and subsequent disruption of the inter-molecular balance needed to keep them stabilized. Once formed, asphaltenes are typically at least as disruptive to flow operations as wax formation. Consequently, measuring wax and asphaltene formation conditions can be an important step to mitigating their flow reduction tendencies.

These PVT and flow assurance properties are typically measured in the laboratory. Drawbacks to the typical laboratory measurements include the time delay involved in laboratory testing and the costs involved with such a delay. For instance, such measurements may not take place for weeks or months after the samples have been collected. Costs for storing and transporting the samples for the laboratory testing can be significant. In addition, the expense of collecting samples can be significant as well for most exploratory environments such as offshore or remote locations. In such environments, only a single opportunity may be available for collecting a sample. Due to such costs and time delay, there is a strong interest in knowing some fundamental PVT and flow assurance characteristics of a freshly captured sample in real time. Other drawbacks include not knowing the quality of a sample or whether a sample was even collected until the expense and delay of laboratory testing has been conducted. The conventional methods of saturation pressure determination in the laboratory include a plot of pressure as a function of sample volume change, with the pressure at which a sharp change in the compressibility occurs defining the saturation pressure. Drawbacks to such conventional methods include the system pressure typically having to be dropped significantly below the saturation pressure in order to define a clear transition point. For some systems, a significant pressure drop below the saturation pressure may result in asphaltene precipitation taking place, which is very difficult to reverse.

Consequently, there is a need for real time testing of hydrocarbon well samples. Other needs include quickly determining whether a sample was collected and its quality. Further needs include a quicker and more cost efficient way to determine PVT information and flow assurance properties of hydrocarbon well samples. In addition, needs include a non-intrusive and non-destructive way to quickly test bottomhole samples.

BRIEF SUMMARY OF SOME OF THE PREFERRED EMBODIMENTS

These and other needs in the art are addressed in one embodiment by a system for testing a fluid, wherein the fluid is disposed within a sample container. The system comprises at least one set of acoustic sensors, wherein the acoustic sensors are disposed about the sample container in a configuration comprising at least one configuration selected from the group consisting of radial and longitudinal, and wherein the at least one set of acoustic sensors generates at least one acoustic signal having a velocity through the fluid. The system further comprises a means for recording and interpreting at least one acoustic signal generated by at least one set of acoustic sensors, wherein the velocity of the at least one acoustic signal indicates information about the fluid system.

In another embodiment, the present invention comprises an apparatus for testing a hydrocarbon sample. The apparatus comprises a sheath disposed about the hydrocarbon sample. In addition, the apparatus comprises at least one set of acoustic sensors, wherein the at least one set of acoustic sensors is secured to the sheath, and further wherein the at least one set of acoustic sensors produces at least one acoustic signal having a velocity through the hydrocarbon sample, wherein the velocity is measured to provide information about the hydrocarbon sample.

A further embodiment of the present invention includes a method for testing a hydrocarbon sample, wherein the hydrocarbon sample is disposed within a container. The method comprises providing at least one set of acoustic sensors. In addition, the method comprises sending at least one acoustic signal through the hydrocarbon sample. Moreover, the method comprises recording a velocity through the hydrocarbon sample of the at least one acoustic signal, wherein the recorded velocity provides information about the hydrocarbon sample.

Other embodiments comprise the acoustic sensors generating signals having a frequency range of 0.1 KHz to 100 GHz. In addition, embodiments include heating the sample to a desired temperature. Moreover, embodiments include using the measured velocity of the signals through the sample to determine the saturation pressure and/or solids deposition point of the sample. Other embodiments include the velocity comprising longitudinal and/or shear velocity.

It will therefore be seen that a technical advantage of the present invention includes an apparatus and method for quickly and efficiently testing hydrocarbon bottomhole samples, thereby eliminating problems encountered by using conventional testing techniques. For instance, problems encountered with the delay and cost of sending samples to a laboratory are overcome. Other problems include not knowing certain information, such as knowing whether a sample was actually taken and knowing the quality of the sample, until the expense and time of sending the sample to the laboratory is undertaken. Such other problems are overcome by the present invention, which can readily determine information such as the location of the piston in the sample chamber and the presence and quantification of water, oil, and gas in the sample chamber. The location of the piston can indicate whether a sample was even collected, while the quantification of the remaining components provides information on the type and quality of the sample collected. The present invention allows this information to be generated on the drilling platform in real time as soon as the bottomhole samples have come to the surface. Such real time testing allows the operator to determine whether additional samples need to be taken and how elaborate the handling of the samples should be prior to additional testing. In addition, the present invention overcomes the problems of asphaltene precipitation with the conventional saturation pressure determination methods by detecting phase transitions substantially at the saturation pressure, which can avoid the asphaltene precipitation.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
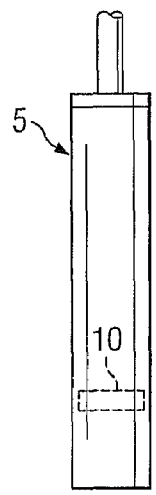
FIG. 1 illustrates a bottomhole sampler.

FIG. 1 illustrates a conventional sampler 5 as is known in the art. The present invention is not limited to the sampler depicted in FIG. 1 but can include any type and shape of sampler that is suitable for containing a sample. Sampler 5 represents a bottomhole sampler for underground reservoirs. Typically, sampler 5 has a piston 10.

Figure 2:
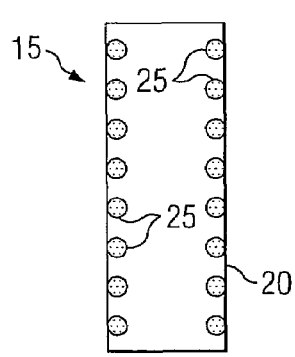
FIG. 2 illustrates an embodiment of an acoustic sample analyzer.

FIG. 2 illustrates an acoustic sample analyzer 15, which comprises a sheath 20 and acoustic sensors 25. Sheath 20 can be made of any suitable material. Without limiting the present invention, examples of suitable materials include metals, plastic, ceramic, and the like. In preferred embodiments, the material is metal. Sheath 20 can also have any suitable thickness. In addition, sheath 20 can have any shape, preferably a shape sufficient to be secured to sampler 5. As the shapes of conventional samplers vary, it is to be understood that the shape of sheath 20 may also vary. For the typical cylindrical shaped sampler, sheath 20 preferably has a cylindrical shape. In some embodiments, sheath 20 is substantially flexible and comprises thin metal or plastic. In alternative embodiments (not illustrated), sheath 20 can comprise at least two separate sections. In some alternative embodiments, such separate sections are connected by hinges, screws, and the like. For example and without limitation, separate sections connected by hinges can be used with thick-walled metal or ceramic construction, which can provide a basis for imbedded heaters or circulating pathways for externally heated heat transfer fluids.

Acoustic sensors are well known in the art, and acoustic sensors 25 can comprise any acoustic sensors suitable for measuring samples. Examples of sensors include Dual Mode P&S [longitudinal-compressional (P) and shear (S)] sensors. Acoustic sample analyzer 15 preferably comprises multiple sets of acoustic sensors 25. In alternative embodiments (not illustrated), acoustic sample analyzer 15 has a single set of acoustic sensors 25. Other alternative embodiments (not illustrated) include acoustic sample analyzer 15 having a single sensor or more than one sensor wherein not all of the sensors are in sets.

Preferably, each set of acoustic sensors 25 has an acoustic signal generator and an acoustic signal receiver. The generator can have any range of frequencies. Preferably, a generator is selected that has a frequency suitable for the desired test conditions. For instance, a frequency is preferably selected that is suitable for the type of metal of sampler 5, the thickness of the walls of sampler 5, and/or the diameter of sampler 5. For a conventional sampler 5 for downhole fluids, one example of a sensor range is 0.1 MHz to 10 MHz. Another example of a sensor frequency is 1.0 MHz. A further example of a sensor frequency is 0.1 kHz to 100 GHz. Acoustic sensors 25 are preferably disposed within sheath 20 in any manner sufficient to allow contact between acoustic sensors 25 and sampler 5. For instance, acoustic sensors 25 can be screwed, welded, glued, pressure fit, and/or embedded to sheath 20.

Figure 3:
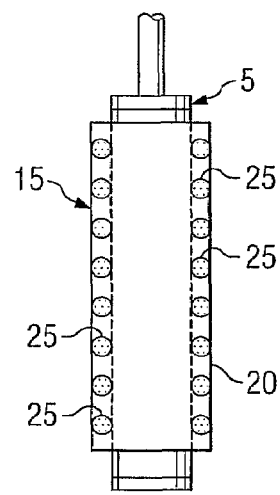
FIG. 3 illustrates an acoustic sample analyzer and a bottomhole sampler.

FIG. 3 illustrates acoustic sample analyzer 15 together with sampler 5. Acoustic sample analyzer 15 is disposed about at least a portion of sampler 5. Acoustic sample analyzer 15 can be secured or unsecured about the at least a portion of sampler 5, preferably secured. Acoustic sample analyzer 15 can be secured by any suitable means such as clamps, bands, and the like. Preferably, acoustic sensors 25 are disposed radially about sampler 5. It is to be understood that the spacing between sets of acoustic sensors 25 and the number of sets of acoustic sensors 25 can be selected to allow for any portion of sampler 5 to be covered. It is to be understood that accuracy of measurements may be improved with closer spacing of acoustic sensors 25. For example, closer spacing may provide a smaller pressure range over which phase transitions can be detected. Closer spacing may also provide improved accuracy with which the volumes of phases can be measured. Preferably, the heads of acoustic sensors 25 are coated with an interface fluid before acoustic sample analyzer 15 is secured to sampler 5. In alternative embodiments, the heads of acoustic sensors 25 are not coated with an interface fluid. In addition, it is preferable but not required that the active face of each acoustic sensor 25 have a curvature that approximates the curvature of the sampler 5. Such a curvature can facilitate the connection between an acoustic sensor 25 and sampler 5.

The signals generated by acoustic sensors 25 can be recorded and/or interpreted by any suitable device such as a microprocessor, data acquisition cards, a central processing unit, plotter, oscilloscope, video, signal receiver, signal generator, analysis software, and the like. In addition, the signals can be transmitted from the acoustic sensors 25 by any suitable means such as signal leads, wireless, and the like. Preferably, the signal is transmitted to the device by signal leads that run from the acoustic sensor 25 to the device.

In alternative embodiments (not illustrated), acoustic sample analyzer 15 can have imbedded heating elements, which can allow acoustic sample analyzer 15 to heat sampler 5. It is preferred that such heating elements be controllable so that the temperature of sampler 5 can be maintained at any desired temperature. In other alternative embodiments (not illustrated), an external heating jacket can be provided to maintain sampler 5 at a desired temperature. The external heating jacket can cover any portion of sampler 5 and acoustic sample analyzer 15, preferably covering substantially all of acoustic sample analyzer 15. Any suitable external heating jacket known in the art can be used. In some embodiments, the external heating jacket can include a thin walled internal and external shell through which externally heated heat transfer fluid is circulated. By adjusting the internal diameter of the internal shell to closely match the external diameter of the sampler 5, heat exchange between the heating jacket and the sampler 5 is maximized so that sampler 5 can be quickly brought to and reasonably maintained at some desired temperature. In an alternate embodiment, the heating element could be a coil or internal passage between the internal and external walls of the heating jacket through which the externally heated heat transfer fluid is circulated. Furthermore, by making the entire heating jacket of some strongly heat conducting material such as copper, the process for heat transfer is facilitated and the heat content of the circulating fluid can be quickly and easily transmitted to adjust and then maintain the temperature of the sampler 5.

In alternative embodiments (not illustrated), acoustic sample analyzer 15 does not have a sheath 20. Instead, at least one set of acoustic sensors 25 is disposed radially or longitudinally about sampler 5. In alternative embodiments, at least one set of acoustic sensors 25 is disposed radially and at least one set of acoustic sensors 25 is disposed longitudinally about sampler 5. In a longitudinal configuration, each acoustic sensor set 25 has one or more sensors on each longitudinal end, with the sender and receiver on opposite or the same ends. The sensors can be secured or unsecured to sampler 5, preferably secured. The sensors can be secured by any suitable means such as screws, bolts, pressure, and the like. Alternatively, each sensor can be used individually for interpretative purposes. In embodiments wherein radial sensors are also used, the longitudinal transducers can be used as the signal generators for the radially positioned transducers. The radial configuration can have several configurations of the sensors. In one embodiment, a single acoustic sensor set 25 can be used with the sensors disposed radially on opposite sides of sampler 5. The acoustic sensor set 25 can then be moved manually or mechanically up and down sampler 5 for detection purposes. In another embodiment for a single sensor set 25, the acoustic sensor set 25 is held fixed, and sampler 5 is moved manually or mechanically up and down between the sensors. More preferable embodiments include more than one set of acoustic sensors 25 disposed radially about sampler 5.

The following is an exemplary application of the present invention as embodied and illustrated on FIGS. 2 and 3. A downhole sample chamber such as a multi-chamber section is located downhole, for instance in a hydrocarbon wellbore operation. The typical downhole sample chamber has more than one sampler 5. After the downhole sample chamber captures a sample, it is pulled out of the hole. Preferably, the samplers 5 are then separated from the downhole sample chamber. An acoustic sample analyzer 15 can be placed around one of the samplers 5 and preferably secured by clamp. Testing of the sample within sampler 5 can include two stages of testing, a quality check stage and/or a test stage. Preferably, the quality check stage is conducted before conducting the test stage. In alternative embodiments, the test stage is conducted before the quality check stage. In other alternative embodiments, only one of the stages is conducted for a given sample.

A quality check can include determining whether a sample was actually taken by the tested sampler 5 and whether the sample is single phase or has multiple phases. If the quality check indicates the presence of more than one phase, it can also indicate the presence and/or quantity of the other phases. For instance, it can indicate the presence and/or quantity of water, the presence and/or quantity of hydrocarbons, and/or the presence and/or quantity of gas. Before activating acoustic sample analyzer 15, the temperature of sampler 5 is adjusted to a desired temperature and optionally maintained at a desired temperature. The temperature can be adjusted by heating elements within acoustic sample analyzer 15 and/or by an external heating jacket. In alternative embodiments, the temperature of acoustic sample analyzer 15 is not adjusted. Acoustic sample analyzer 15 is then activated. Preferably, sampler 5 is substantially vertical during the testing. It is preferred that acoustic sample analyzer 15 is operated as a constantly cycling device (e.g., acoustic sensors 25 ping repeatedly). Such a constantly cycling device can allow substantially immediate detection and interpretation of the sample. In alternative embodiments, acoustic sample analyzer 15 is not operated as a constantly cycling device. For example, acoustic sample analyzer 15 can be operated as an intermittent cycling device in which the intermittent cycling can be dictated by the availability of portable power and the rate at which the device drains the power.

Figure 4:
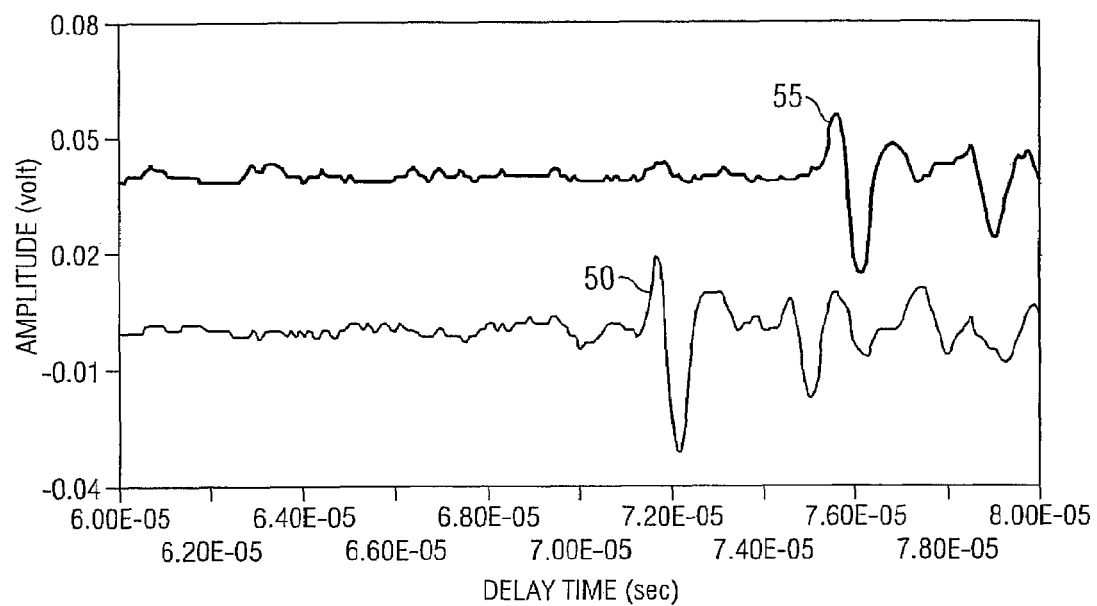
FIG. 4 illustrates the delay time versus the amplitude of an acoustic signal through a sample.
Figure 5:
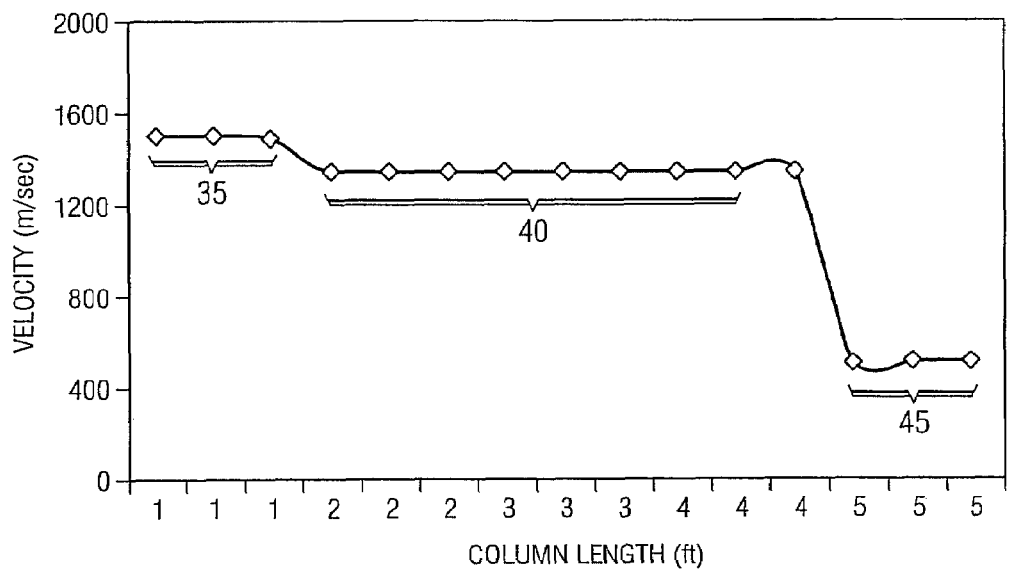
FIG. 5 illustrates velocity of the acoustic signal through a sample column length.
Figure 6:
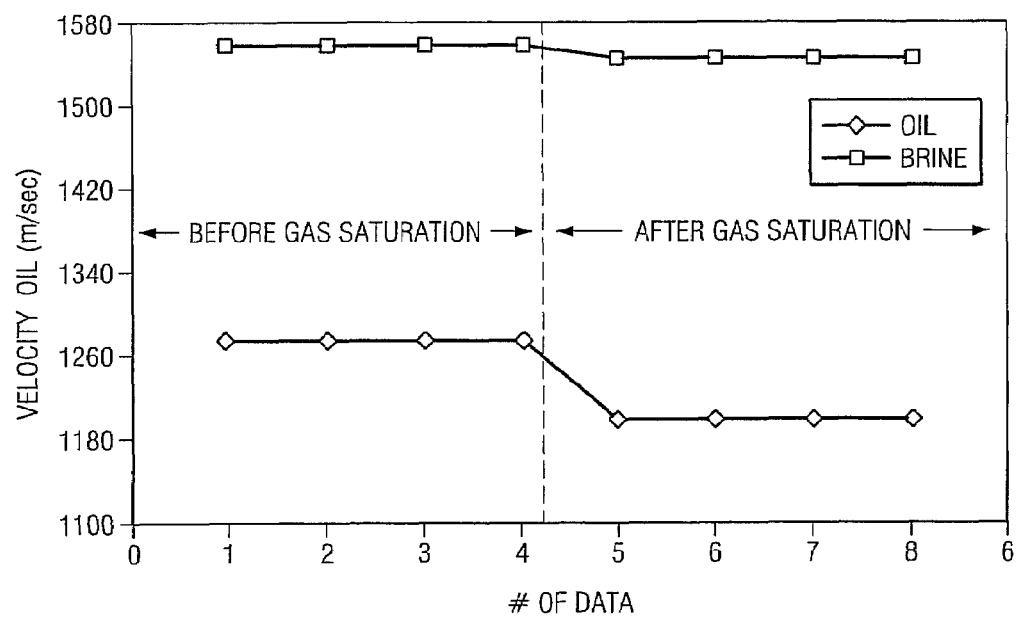
FIG. 6 illustrates the effect of gas saturation on acoustic velocity.

When acoustic sample analyzer 15 is activated, acoustic sensors 25 are activated, and their signals are recorded. The velocity of the sample is recorded. The velocity can be longitudinal and/or shear velocity. Both longitudinal and shear velocity include information on the arrival time and amplitudes of the wave form. A plot of the measured velocity as a function of the length of column in sampler 5 can be generated. An example of such a plot is illustrated in FIG. 5. FIG. 5 indicates the presence and height 35 of a column of water above piston 10, the presence and height of a liquid hydrocarbon 40 above piston 10, and the presence and height of a gas 45 above piston 10. The presence of gas, liquid hydrocarbon, and water can be differentiated by the velocity of the acoustic signal through the sample. For instance, water is a faster conductor of the acoustic signal than liquid hydrocarbon and gas, and the liquid hydrocarbon is a faster conductor of the acoustic signal than the gas. FIG. 4 is an illustration of the arrival time of acoustic signals through liquid hydrocarbon and water. It can be seen that the arrival time 50 of an acoustic signal through water is faster than the arrival time 55 of an acoustic signal through liquid hydrocarbon. It should be understood that even though FIG. 4 is illustrated showing water 50 and liquid hydrocarbons 55, the present invention can also be used for gas saturated systems. FIG. 6 is an illustration of saturation of a brine and oil phase with gas. It can be seen that the gas increases the differentiation of the oil and brine. Therefore, as the differentiation in velocity can be used in the present invention to differentiate between phases, acoustic sample analyzer 15 is viable for gas saturated systems as well.

A plot as illustrated in FIG. 5 can provide a substantially instantaneous indication of the quality of the sample in sampler 5 or can improve the quality of the sampling by allowing the operator to move the sampling point lower out of a gas zone and into an oil zone if, for instance, an oil sample is desired. For instance, the location of piston 10 can indicate whether a sample was taken and can also indicate whether a partial sample was taken. As an example, if piston 10 was stuck during collection with no sample taken, a plot may show a substantially flat line with the piston 10 located at the top of sampler 5. In regards to water, its presence and quantity may indicate the overall quality of the sample and may also provide information as to the nature of the downhole conditions when the sample was taken. In regards to the liquid hydrocarbon, its presence and quantity can provide information such as whether an insufficient hydrocarbon sample was collected. As an example, if excess water was collected, a plot may show that an insufficient amount of liquid hydrocarbon was collected to obtain a sufficient test of the downhole conditions. Such information about the liquid hydrocarbon sample can allow the avoidance of sample reconditioning, transfer, and long term storage costs of the sample. The presence and quantity of a gas may be indicative of poor sample gathering practice or proximity to a gas cap, which can allow corrective action to be taken to improve the interpretation of the gas phase.

In the test stage, PVT information such as CCE and/or solids onset (such as wax, asphaltene, and the like) can be indicated. With acoustic sample analyzer 15 attached to sampler 5, the temperature of the sample can be adjusted and optionally maintained at a desired temperature. The temperature can be adjusted by heating elements within acoustic sample analyzer 15 and/or by an external heating jacket. In alternative embodiments, the temperature is not adjusted. In some instances, it may be desired to adjust the pressure and/or rock sampler 5 before conducting the test stage. For instance, if it is indicated in the quality check stage that gas in the sample has separated from the liquid, pressure can be added to sampler 5 to increase the pressure of the sample. The pressure of sampler 5 can be monitored and/or increased by any suitable method. For example, the pressure can be monitored by pressure gauge or any other suitable device, and the pressure can be increased by attaching a fluid pump to the hydraulic displacement fluid located under piston 10 and injecting additional hydraulic displacement fluid under piston 10, which can pressurize the sample to single phase. Rocking sampler 5 may facilitate the sample to equilibrate to a single phase. Rocking samples is well known in the art, and sampler 5 can be rocked by any suitable means. For instance, sampler 5 can be rocked by manual rocking, a motorized rocking stand, and the like. In some embodiments, the sample is rocked until it is sufficiently homogenized. In alternative embodiments, non-rocking means may be used to mix the sample. Such non-rocking means can include sonic horns. A sonic horn is conventionally used to translate electrical energy into acoustic vibrations that can be used to vigorously mix a liquid system. With the sample in a single phase, a plot of the measured longitudinal velocity signal can be indicated as a substantially flat line, which is indicative of a single phase.

After the sample is sufficiently pressurized and at the desired temperature, a fixed volume of the fluid below piston 10 is removed from sampler 5, preferably at constant temperature. The fluid can be removed by any suitable method. For instance, some of the fluid can be drained into a graduated cylinder for measurement. A preferable method is to attach a fluid pump to the hydraulic displacement fluid located under piston 10. The fluid can be displaced by backing off on the pump. Such an approach can allow for a measured amount of the fluid to be removed. Optionally, sampler 5 can be rocked after each volume adjustment step, which may facilitate the sample to equilibrate.

After the fixed volume of fluid is removed, acoustic sensors 25 transmit their signals through the sample. It is indicated by the measured acoustic sensor 25 signals whether there is any phase change in the sample such as gas release or solids formation. For instance, with a gas release, the measured signal, such as the longitudinal velocity, can be attenuated, which indicates the presence of a phase transition. It is to be understood that the measurements can be made whether the sample is being rocked or held steady. When gas phase volume measurements are made, the rocking is preferably stopped, and sampler 5 is placed substantially vertical, which can allow for partitioning of the multiple phases. If the first volume adjustment step does not provide an indication of a phase transition (such as attenuated longitudinal velocity readings), it can be repeated, with appropriate volumes being removed until a phase transition is observed.

For liquid hydrocarbons, phase transition can be in the form of gas bubbles released at the bubble point and/or solids deposition. For example, if the initial attenuation of the signal is due to gas released at the saturation pressure, then, with time, the attenuation will disappear, while with successive volume expansion steps a gas zone at the top of the sample cylinder will be indicated by the measured signals (e.g., a slower longitudinal velocity will be indicated at the top of sampler 5). However, if the initial signal attenuation was due to solids deposition, then successive volume expansion steps will not show a gas zone, and the signal will remain attenuated due to the presence of suspended solids in the sample. In embodiments wherein the sample is a single phase gas (e.g., as for a condensate), the first phase transition observed may be a dew point transition as liquid comes out of solution. Therefore, acoustic sample analyzer 15 can be used to detect a saturation pressure and/or a solids deposition point.

In some instances, substantially all of the fluid below piston 10 may have been removed during sampling or during the volume adjustment steps, but no phase change may have occurred during the volume adjustment next step. With sampler 5 preferably in a vertical position, piston 10 may be disposed at the bottom of sampler 5 in such instances. It is to be understood that because no further expansion of the sample is possible, the phase change can only be observed by repeating the volume expansion step starting with a smaller sample volume. To achieve a smaller sample volume, a portion of the sample may be removed. Preferably, the sample volume is reduced in the single phase condition, which can preserve the integrity of the sample. Preferably, a liquid is injected at the bottom of sampler 5 to move up piston 10 to pressurize the sample and maintain a single phase condition during the removal step. The liquid is preferably water. A corresponding amount of the single phase fluid is taken out of the top of sampler 5. The volume adjustment steps can then be repeated until a phase change occurs. In alternative embodiments, liquid is not added to below piston 10 but only the single phase fluid in sampler 5 is removed. In such alternative embodiments, continued removal of sample from the system may drop the pressure below the saturation pressure and a detectable gas or liquid phase may be generated. In such alternative embodiments, the volume adjustment steps are repeated until a phase change occurs.

The determination of saturation pressures for a liquid hydrocarbon sample can be used for equation of state simulations. For instance, heating and optionally rocking of sampler 5 can allow for saturation pressures at a variety of temperatures to be determined. After the saturation pressure is determined for a given temperature, the sample can be heated and maintained at another temperature. At such temperature, the testing stage can be conducted to determine the saturation pressure at such temperature.

It is to be understood that other information can be determined as well by using acoustic sample analyzer 15. For instance, as the sample pressure is lowered below the saturation point, gas can be released from solution. Acoustic sample analyzer 15 can be used to determine the volumes of the water, gas, and liquid hydrocarbons in such a sample. For instance, the longitudinal velocity of the acoustic signals through the sample can indicate the presence and volume of each, as can be shown by the plot of FIG. 5. It is to be understood that the accuracy of the measurements can be a function of factors such as the resolution of the transducers and their spacing.

In alternative embodiments (not illustrated), acoustic sample analyzer 15 can also be used for differentiating between rich and dry gas (e.g., methane). It is to be understood that an acoustic signal can travel through rich gas faster than dry gas. Therefore, a recording of the velocity through a gas can indicate whether it is a dry or rich gas based upon the indicated signals of acoustic sensors 25.

It is to be understood that the acoustic sample analyzer 15 of the present invention is not limited to testing hydrocarbons but can test any fluid. For instance, it can be used to test water quality in water wells. In such instances, the longitudinal velocity of acoustic signals through a water sample from a well can indicate whether the sample has different phases. It can also be used to test contaminants.

Although the present invention and its advantages have been described in detail, it should be understood that various changes, substitutions and alterations may be made herein without departing from the spirit and scope of the invention as defined by the appended claims.

What is claimed is:

1. A method comprising:
    drawing formation fluids into a sample container, the sample container disposed within a borehole;
    retrieving the sample container from the borehole; and then
    surrounding the sample container with a sheath having at least one set of acoustic transducers;
    generating at least one acoustic signal having a velocity through fluid in the sample container; and
    determining phase information of the fluid based at least in part on said velocity.

2. The method of claim 1, wherein said determining includes:
    measuring said velocity as a function of position in the sample container.

3. The method of claim 2, wherein said measuring includes moving the acoustic transducers relative to the sample container.

4. The method of claim 1, further comprising:
    determining a bubble point of the fluid.

5. The method of claim 1, further comprising:
    determining a solids onset point for the fluid.

6. A method comprising:
    retrieving a sample container from a borehole;
    surrounding the sample container with a sheath having at least one set of acoustic transducers;
    generating at least one acoustic signal having a velocity through fluid in the sample container;
    determining phase information based at least in part on said velocity; and
    moving a piston within the sample container to measure pressure, volume and temperature properties of the fluid.

7. The method of claim 6, further comprising:
    heating the sample container using heaters embedded in the sheath.

8. The method of claim 6, wherein said determining includes:
    measuring said velocity as a function of position in the sample container.

9. The method of claim 8, wherein said measuring includes moving the acoustic transducers relative to the sample container.

10. The method of claim 6, further comprising:
    determining a bubble point of the fluid.

11. The method of claim 6, further comprising:
    determining a solids onset point for the fluid.

12. The method of claim 6, further comprising:
    drawing the fluid into the sample container by movement of the piston.

13. The method of claim 1, further comprising:
    heating the sample container using heaters embedded in the sheath.

* * * * *